United States Patent
Karbeyaz et al.

(10) Patent No.: US 10,388,000 B2
(45) Date of Patent: Aug. 20, 2019

(54) NOISE REDUCTION IN RADIATION IMAGE

(71) Applicant: Analogic Corporation, Peabody, MA (US)

(72) Inventors: Basak Ulker Karbeyaz, Concord, MA (US); Kevin Cheng, Lexington, MA (US); Charles Shaughnessy, Hamilton, MA (US); David Rozas, Brighton, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 15/511,267

(22) PCT Filed: Sep. 15, 2014

(86) PCT No.: PCT/US2014/055564
§ 371 (c)(1),
(2) Date: Mar. 15, 2017

(87) PCT Pub. No.: WO2016/043691
PCT Pub. Date: Mar. 24, 2016

(65) Prior Publication Data
US 2017/0249723 A1    Aug. 31, 2017

(51) Int. Cl.
*G06K 9/00*    (2006.01)
*G06T 5/00*    (2006.01)
*A61B 6/00*    (2006.01)

(52) U.S. Cl.
CPC ............ *G06T 5/002* (2013.01); *A61B 6/5258* (2013.01); *G06T 2207/10072* (2013.01); *G06T 2207/10081* (2013.01)

(58) Field of Classification Search
None
See application file for complete search history.

(56) References Cited

U.S. PATENT DOCUMENTS

| 4,926,871 | A | * | 5/1990 | Ganguly | ............... A61B 5/204 600/443 |
| 5,500,904 | A | * | 3/1996 | Markandey | ............ G06T 7/269 382/103 |

(Continued)

OTHER PUBLICATIONS

International Search Report cited in related application No. PCT/US14/55564 dated May 29, 2015, pp. 14.

(Continued)

*Primary Examiner* — Samah A Beg
(74) *Attorney, Agent, or Firm* — TraskBritt

(57) ABSTRACT

Among other things, one or more techniques and/or systems are described for processing images yielded from an examination via radiation to reduce visible noise in the images. After an image is reconstructed, a noise contribution to the image (e.g., an amount of noise in the image) is estimated to determine a target noise contribution for the image. The target noise contribution for the image may vary based upon, among other things, dose of radiation, aspects or properties of an object being imaged, etc. The image is subsequently filtered using one or more filtering techniques to generate a filtered image, and a noise contribution to the filtered image is determined. When the noise contribution to the filtered image satisfies the target noise contribution (e.g., a sufficient amount of noise has been filtered out of the image), the filtered image is combined with the reconstructed image to generate a blended image.

20 Claims, 4 Drawing Sheets

(56) References Cited

U.S. PATENT DOCUMENTS

| | | | | |
|---|---|---|---|---|
| 5,841,829 | A * | 11/1998 | Dolazza | A61B 6/032 378/11 |
| 6,449,330 | B1 * | 9/2002 | Li | A61B 6/032 378/15 |
| 6,813,374 | B1 * | 11/2004 | Karimi | G01V 5/0008 378/207 |
| 8,818,109 | B2 * | 8/2014 | Kisilev | G06K 9/40 382/132 |
| 9,361,717 | B2 * | 6/2016 | Zomet | G06T 11/60 |
| 2004/0161141 | A1 * | 8/2004 | Dewaele | G06K 9/3208 382/132 |
| 2006/0204065 | A1 * | 9/2006 | Hsieh | G06T 11/005 382/128 |
| 2007/0165921 | A1 * | 7/2007 | Agam | G06T 7/0012 382/128 |
| 2008/0095462 | A1 | 4/2008 | Hsieh et al. | |
| 2008/0310751 | A1 * | 12/2008 | Rai | G06T 5/002 382/264 |
| 2012/0106815 | A1 | 5/2012 | Yang et al. | |
| 2012/0183195 | A1 * | 7/2012 | Mercur'ev | G06T 5/002 382/132 |
| 2012/0224784 | A1 * | 9/2012 | Cohen | G06T 5/002 382/260 |
| 2014/0341466 | A1 * | 11/2014 | Babacan | G06T 5/002 382/163 |
| 2015/0069255 | A1 * | 3/2015 | Abraham | G01T 1/17 250/393 |
| 2016/0015357 | A1 * | 1/2016 | Rozas | A61B 6/032 378/207 |
| 2017/0091935 | A1 * | 3/2017 | Leon | A61B 6/032 |
| 2018/0025513 | A1 * | 1/2018 | Sakimoto | A61B 6/03 382/132 |
| 2018/0211132 | A1 * | 7/2018 | Shiraishi | G06K 9/6215 |

OTHER PUBLICATIONS

Panda, et al., "Filtering and Performance Evaluation for Restoration of Grayscale Image Corrupted by Salt & Paper Noise Using Low Pass Filtering Schemes", Emerging Trends in Engineering and Technology (ICETET), 2009 2nd International Conference ON, IEEE, Piscataway, NJ, USA, Dec. 16, 2009, pp. 1-6.

Zhang, et al., "Multiple-step local Wiener filter with proper stopping in wavelet domain", Journal of Visual Communication and Image Representation, vol. 25, No. 2, Nov. 26, 2013, pp. 1-9.

EP Office Action cited in EP Application No. 14777982.1 dated Jan. 8, 2019, 8 pgs.

* cited by examiner

NOISE REDUCTION IN RADIATION IMAGE

CROSS-REFERENCE TO RELATED APPLICATIONS

This application is a national phase entry under 35 U.S.C. § 371 of International Patent Application PCT/US2014/055564, filed Sep. 15, 2014, designating the United States of America and published in English as International Patent Publication WO 2016/043691 A1 on Mar. 24, 2016, which claims the benefit under Article 8 of the Patent Cooperation Treaty to French Patent Application Serial No. 1652768, filed Mar. 31, 2016.

BACKGROUND

This disclosure relates to reducing noise in images reconstructed from data acquired during an examination of an object via ionizing radiation, such as x-rays or gamma rays. It finds particular application in medical environments where dosage to a patient is monitored, however it may also find applicability in security, industrial, and/or other applications where noise reduction in reconstructed images is desirable.

Today, radiation imaging systems such as computed tomography (CT) systems, single-photon emission computed tomography (SPECT) systems, digital projection systems, and/or line-scan systems, for example, are useful to provide information, or images, of interior aspects of an object under examination. The object is exposed to rays of radiation photons (e.g., x-ray photons, gamma ray photons, etc.) and radiation photons traversing the object are detected by a detector array positioned substantially diametrically opposite a radiation source relative to the object. A degree to which the radiation photons are attenuated by the object (e.g., absorbed, reflected, etc.) is measured to determine one or more properties of the object, or rather aspects of the object. For example, highly dense aspects of the object typically attenuate more radiation than less dense aspects, and thus an aspect having a higher density, such as a bone or metal, for example, may be apparent when surrounded by less dense aspects, such as tissue or clothing.

Noise is inherently introduced into the system when measuring or sampling photons or rather when measuring/sampling charge generated from photons impinging the detector array. This noise is sometimes referred to as photon noise, and artifacts (e.g., streaking, blurring, etc.) in images generated from an examination are sometimes attributable, at least in part, to this photon noise. Accordingly, the photon noise may reduce the quality of an image.

Due to quantum statistics, the photon noise level (e.g., ratio of photon noise to useful signal) generated from an examination of an object is inversely related to the dose of radiation applied to the object. For example, the photon noise level increases as the dose applied to the object decreases. Accordingly, in some applications, the dose of radiation applied to the object is balanced with the desire for images having few to no artifacts.

BRIEF SUMMARY

Aspects of this disclosure address the above matters, and others. According to an aspect, a method for processing images yielded from an examination via radiation is provided. The method comprises receiving an image of an object that has been exposed to radiation, where the image is generated based upon an interaction between the radiation and the object. The method also comprises estimating a first noise contribution to the image to derive a target noise contribution and filtering the image to generate a first filtered image. The method further comprises estimating a second noise contribution to the first filtered image and comparing the target noise contribution to the second noise contribution to determine whether the target noise contribution has been satisfied by the filtering.

According to another aspect, a computer-readable medium comprising processor-executable instructions that when executed perform a method is provided. The method comprises estimating a first noise contribution to an image yielded from a radiation examination of an object to derive a target noise contribution and filtering the image to generate a first filtered image. The method also comprises estimating a second noise contribution to the first filtered image and comparing the target noise contribution to the second noise contribution to determine whether the target noise contribution has been satisfied by the filtering. The method further comprises combining the first filtered image with the image when, responsive to the comparing, the target noise contribution has been satisfied by the filtering.

According to yet another aspect a radiation imaging system is provided. The radiation imaging system includes a radiation source configured to expose an object under examination to radiation and a detector array configured to produce one or more signals based upon detecting at least some of the radiation that traverses the object. The system also comprises an image reconstruction component configured to reconstruct an image based upon the one or more signals and a noise reduction component. The noise reduction component is configured to estimate a first noise contribution to the image to derive a target noise contribution, filter the image to generate a first filtered image, and estimate a second noise contribution to the first filtered image. The noise reduction component is also configured to compare the target noise contribution to the second noise contribution to determine whether the target noise contribution has been satisfied by the filtering and combine the first filtered image with the image when, responsive to the comparing, the target noise contribution has been satisfied by the filtering.

Those of ordinary skill in the art will appreciate still other aspects of this disclosure upon reading and understanding the appended description.

BRIEF DESCRIPTION OF THE DRAWINGS

The application is illustrated by way of example and not limitation in the figures of the accompanying drawings, in which like references generally indicate similar elements and in which.

DETAILED DESCRIPTION

Figure 1:
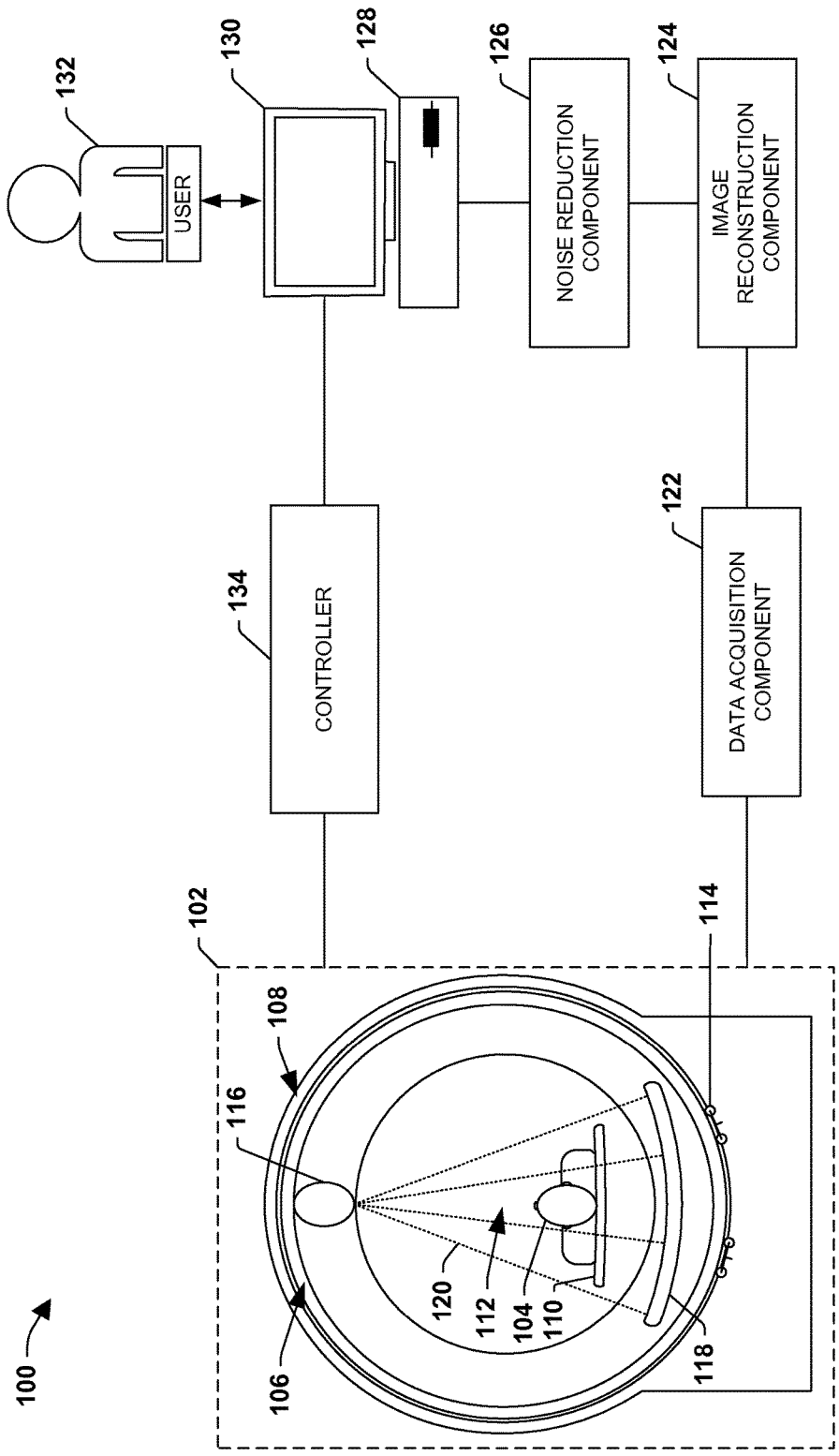
FIG. 1 illustrates an example environment of a radiation imaging system.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

According to some embodiments, systems and/or techniques for reducing artifacts, caused by photon noise, in post-reconstruction images are provided. An image, which may be a two-dimensional image or a three-dimensional image is received and the amount of noise, or a first noise contribution, in the image is estimated. Based upon this estimation, a desired noise target, or target noise contribution, for the image is computed. For example, it may be desirable to remove 20% of the noise from the image, such that the image is merely 80% 'noisy.' One or more noise reduction filters are then applied to the image and/or to respective pixels thereof to reduce the noise and/or to more evenly distribute the noise amongst pixels. The resulting image may be referred to as a filtered image, and an amount of noise, or a second noise contribution, in the filtered image is estimated using one or more noise estimation techniques. The estimation of the noise in the filtered image, or the second noise contribution, is compared to the desired noise target, or the target noise contribution, to determine if the desired noise target has been satisfied by the filtering (e.g., has the filtering sufficiently reduced the noise in the image).

If the desired noise target has not been satisfied, at least some of the one or more noise reduction filters are applied to the filtered image to generate a second filtered image. The amount of noise in this second filtered image, or a third noise contribution, is estimated, and the estimation of the noise in the second filtered image is compared to the desired noise target to determine if the desired noise target has been satisfied (e.g., is the image now sufficiently less noisy). Such a process may be iteratively repeated until the desired noise target has been satisfied and/or until some other stopping criteria has been satisfied (e.g., the process has been repeated at least a specified number of times).

When the desired noise target has been satisfied and/or the other stopping criteria has been satisfied, the most recently generated filtered image is blended with the original image (e.g., the post-reconstruction image) to generate a blended image. For example, a value of a first pixel of the original image is merged (e.g., averaged) with a value of a corresponding pixel of the most recently generated filtered image to generate a value for a first pixel of the blended image. In some embodiments, a contribution of the original image to the blended image is weighted equally with a contribution of the most recently generated filtered image to the blended image. In some embodiments, the contribution of the original image is weighted differently than the contribution of the most recently generated filtered image to the blended image. Accordingly, a value for a first pixel of the blended image may be an average of a first weighted value of the first pixel in the original image and a second weighted value of the first pixel in the most recently generated filtered image, where a first weight is applied to a value of the first pixel in the original image to generate the first weighted value and a second weight is applied to a value of the first pixel in the most recently generated filtered image to generate the second weighted value, where the first weight may be the same as or different than the second weight.

FIG. 1 illustrates a radiation imaging system 100 where the techniques and/or systems described herein may be employed. In the illustrated embodiment, the radiation imaging system 100 is a computed tomography (CT) system, although the systems and/or techniques described herein may find applicability to other radiation imaging systems such as line-scan systems, mammography systems, and/or diffraction systems, for example. The radiation imaging system 100 thus merely provides an example arrangement and is not intended to be interpreted in a limiting manner, such as necessarily specifying the location, inclusion, and/or relative position of the components depicted therein. By way of example, in some embodiments, a data acquisition component 122 is part of a detector array 118 and/or is located on a rotating gantry 106 of an examination unit 102.

In the example radiation imaging system 100, the examination unit 102 is configured to examine objects 104. The examination unit 102 comprises the rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). During an examination of an object 104, the object 104 is placed on a support article 110, such as a bed or conveyor belt, for example, and positioned within an examination region 112 (e.g., a hollow bore in the rotating gantry 106), where the object 104 is exposed to radiation 120.

The rotating gantry 106 may surround a portion of the examination region 112 and may comprise a radiation source 116 (e.g., an ionizing radiation source such as an x-ray source and/or gamma-ray source) and the detector array 118. The detector array 118 is typically mounted on a substantially diametrically opposite side of the rotating gantry 106 relative to the radiation source 116, and during an examination of the object 104, the rotating gantry 106 (e.g., including the radiation source 116 and detector array 118) is rotated about the object 104. Because the radiation source 116 and the detector array 118 are mounted to a same rotating gantry 106, a relative position between the detector array 118 and the radiation source 116 is substantially maintained during the rotation of the rotating gantry 106.

During the examination of the object 104, the radiation source 116 emits cone-beam and/or fan-beam radiation configurations from a focal spot of the radiation source 116 (e.g., a region within the radiation source 116 from which radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or multiple energy spectrums depending upon, among other things, whether the radiation imaging system 100 is configured as a single-energy system or a multi-energy (e.g., dual-energy) system.

As the emitted radiation 120 traverses the object 104, the radiation 120 may be attenuated differently by different aspects of the object 104. Because different aspects attenuate different percentages of the radiation 120, the number of photons and/or energy levels of respective photons detected by detector cells of the detector array 118 may vary. For example, more dense aspects of the object(s) 104, such as a bone, may attenuate more of the radiation 120 (e.g., causing fewer photons to impinge upon a region of the detector array 118 shadowed by the more dense aspects) than less dense aspects, such as tissue.

Radiation detected by the detector array 118 may be directly converted and/or indirectly converted into analog signals that can be transmitted from the detector array 118 to the data acquisition component 122 operably coupled to the detector array 118. The analog signal(s) may carry information indicative of the radiation detected by the detector array 118 (e.g., such as an amount of charge measured over a sampling period and/or an energy level of detected radiation) as well as photon noise that, due to quantum statistics, is inherently associated with detecting photons.

The data acquisition component 122 is configured to convert the analog signals output by the detector array 118 into digital signals and/or to compile signals that were transmitted within a predetermined time interval, or measurement interval, using various techniques (e.g., integration, photon counting, etc.). The compiled signals are typically in projection space and are, at times, referred to as projections. A projection may be representative of the information collected or measurements acquired by respective detector cells of the detector array 118 during an interval of time or a view, where a view corresponds to data collected while the radiation source 116 was at a particular view-angle or within a particular angular range relative to the object 104.

The projections generated by the data acquisition component 122 may be transmitted to an image reconstruction component 124 operably coupled to the data acquisition component 122. The image reconstruction component 124 is configured to convert at least some of the data from projection space to image space using suitable analytical, iterative, and/or other reconstruction techniques (e.g., tomosynthesis reconstruction, back-projection, iterative reconstruction, etc.). The images generated by the image reconstruction component 124 (e.g., at times referred to as post-reconstruction images) may be in two-dimensional space and/or three-dimensional space and may be representative of the degree of attenuation through various aspects of the object 104 for a given view, may be representative of the density of various aspects of the object 104, and/or may be representative of the z-effective of various aspects of the object 104, for example.

In some embodiments, due to among other things, the photon noise inherently introduced into the system when detecting photons, at least some images generated by the image reconstruction component 124 may comprise artifacts that blur, streak, etc. a portion of the image, conceal a portion of the object 104 within the image, and/or otherwise reduce the quality and/or diagnostic usefulness of the image.

Accordingly, at least some images generated by the image reconstruction component 124 are transmitted to a noise reduction component 126 configured to reduce the degree of visible noise within the image (e.g., thus reducing artifacts in the image) by applying one or more filters to the image to generate a filtered image. In some embodiments, this filtered image is blended with the image received from the image reconstruction component 124 to generate a blended image, where pixel values in the blended image are yielded by merging pixel values of the image received from the image reconstruction component 124 with pixel values of the filtered image. In some embodiments, by blending the image received from the image reconstruction component 124 (e.g., at times referred to as an original image) with the filtered image, edges of features within the object are substantially maintained while the visible noise in the image is substantially reduced relative to the original image to improve image quality (e.g., by reducing artifacts) and/or to improve diagnostic usefulness, for example.

The example radiation imaging system 100 further comprises a terminal 128, or workstation (e.g., a computer), that may be configured to receive blended images output by the noise reduction component 126 and/or to receive images output by the image reconstruction component 124, which may be displayed on a monitor 130 to a user 132 (e.g., security personnel, medical personnel, etc.). In this way, the user 132 can inspect the image(s) to identify areas of interest within the object 104, for example. The terminal 128 can also be configured to receive user input which can direct operations of the examination unit 102 (e.g., a speed to rotate, a speed and direction of the support article 110, etc.), for example.

In the example radiation imaging system 100, a controller 134 is operably coupled to the terminal 128. The controller 134 may be configured to control operations of the examination unit 102, for example. By way of example, in one embodiment, the controller 134 may be configured to receive information from the terminal 128 and to issue instructions to the examination unit 102 indicative of the received information (e.g., change the position of the support article relative to the radiation source 116, etc.).

Figure 2:
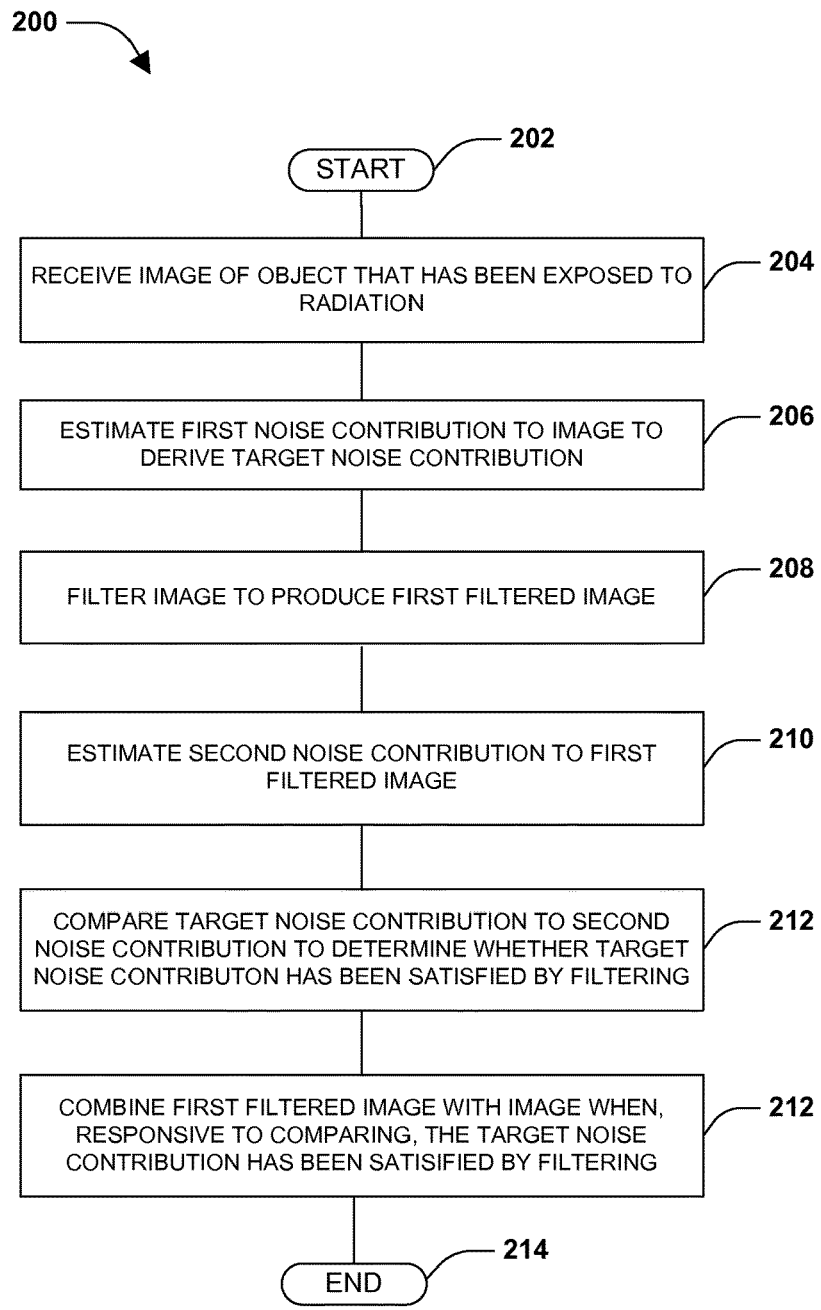
FIG. 2 is a flow diagram illustrating an example method for processing images yielded from an examination via radiation.

Referring to FIG. 2, an example method 200 for post-reconstruction image filtering is provided. The method begins at 202 and an image of an object is received at 204. The image is produced by exposing the object to ionizing radiation, such as x-rays or gamma rays, and measuring/detecting x-rays that traverse the object. In some embodiments, the image is a two-dimensional image and respective pixels represent a degree of attenuation through the object. In other embodiments, the image is a three-dimensional image and respective voxels represent a density, z-effective, or other property of a portion of the object. For purposes of this disclosure, unless otherwise explicitly noted, the term pixel is meant to refer to or comprise both a two-dimensional pixel and a three-dimensional voxel.

In some embodiments, the image that is received at 202 comprises artifacts and/or other features that reduce the quality of the image and/or the diagnostic usefulness of the image by smearing or otherwise distorting aspects of the object, concealing aspects of the object, etc. At least some of these artifacts may be attributable to noise in the image, such as yielded from photon noise introduced during the detection of radiation photons.

At 206 in the example method 200, a noise contribution to the image (e.g., at times referred to herein as a first noise contribution) is estimated to derive a target noise contribution. In some embodiments, the noise contribution to the image is estimated by computing the spatial derivative of respective pixels in one or more dimensions. By way of example, where the image is a three-dimensional image, the spatial derivative of a value of the pixel (e.g., at times referred to as a CT number or a Hounsfield value of the pixel) in the x dimension and in the y dimension is computed (e.g., where an x,y plane generally corresponds to a plane in which the rotating gantry 106 is rotated). In some embodiments, the median value of at least some of these spatial derivatives is subsequently computed and this median value is weighted with respect to one or more reconstruction parameters (e.g., parameters defined when reconstructing the image) to determine the noise contribution to the image. In some embodiments, a robust median estimator is used to estimate the noise in the image, where one or more parameters of the robust median estimator are based upon (e.g., a function of) parameters of an image reconstruction algorithm utilized to reconstruct the image.

In some embodiments, prior to computing the median value, pixels are classified or grouped based upon the value of respective pixels. By way of example, in an examination of a patient, pixels with a value in the range of −100 to 100 Hounsfield Units (HU) may be typically representative of tissue (e.g., veins, organs, etc.) while pixels having a value outside of this range may be typically representative of non-tissue (e.g., bones, air, implants, etc.). In some embodiment, merely the spatial derivatives of those pixels having a value in the range of −100 to 100 HU are considered when computing the median value. Accordingly, the spatial derivative of pixels having a value outside of the range, and thus likely to be representative of non-tissue, are not factored in when estimating the noise in the image.

At 208 in the example method 200, the image is filtered to generate a first filtered image. One or more filtering techniques may be applied to the image to generate the filtered image. By way of example, in some embodiments, an outlier filter, such as a 3D outlier filter, is applied to the image. The outlier filter is configured to compare a first pixel to a set of pixels neighboring the first pixel and to adjust one or more properties of the first pixel based upon properties of the set of pixels neighboring the first pixel if the one or more properties of the first pixel deviate substantially from the properties of the set of pixels.

As an example of a 3D outlier filter, respective pixels of the image may be associated with a value, such as a CT value. During a 3D outlier filtering process, a mean pixel value of a set of pixels neighboring a first pixel may be computed. This mean pixel value may be non-weighted or weighted (e.g., where the values of pixels immediately adjacent the first pixel are assigned a weight that is different than a weight that is assigned to the values of pixels that are separated from the first pixel by at least one pixel). A value of the first pixel may be compared to the mean pixel value to determine a deviation value for the first pixel. If the deviation value exceeds a deviation threshold, the mean pixel value may be applied to the first pixel. In this way, the original value of the first pixel (e.g., as computed during image reconstruction) is replaced with the mean pixel value of the set of pixels neighboring the first pixel.

Such a process of comparing the value of a pixel to a mean pixel value for a set of pixels neighboring the pixel may be repeated for a plurality of pixels in the image.

In some embodiments, the deviation threshold is varied between pixels of the image. By way of example, the deviation threshold for a pixel may be set as a function of a value of the pixel when the image was received at 204. By way of example, if the value of the pixel is in a pixel value range of −100 to 100 HU (e.g., and thus the pixel is likely to be representative of tissue), the deviation threshold may be set to a first deviation threshold (e.g., 1 sigma, such that a deviation value that exceeds 1 sigma causes the mean pixel value, for a set of pixels neighboring the pixel, to be applied to the pixel). If the value of the pixel is not in the pixel value range of −100 to 100 HU (e.g., and thus the pixel is not likely to be representative of tissue), the deviation threshold may be set to a second deviation threshold (e.g., 3 sigma, such that a deviation value that exceeds 3 sigma causes the mean pixel value, for a set of pixels neighboring the pixel, to be applied to the pixel). In this way, pixels representative of tissue, which may be expected to have little to no deviation if no noise is present, are treated differently than pixels representative of non-tissue, which may naturally have greater deviation in the pixel values due to variations in the density, z-effective, etc. of non-tissue features of an object, for example.

In may be appreciated that due to edges in an object (e.g., due to a transition from tissue to a bone, for example), at least some pixels may have a value that substantially differs from the values of neighboring pixels. Accordingly, in some embodiments, an upper deviation threshold may be defined as well. In such embodiments, the mean pixel value of a set of pixels neighboring a pixel may be applied to the pixel if the deviation value for the first pixel is between the deviation threshold and the upper deviation threshold. For example, the deviation threshold and the upper deviation threshold may be set at 1 sigma and 3 sigma, respectively, for a pixel having a value in the range of −100 to 100 HU. If the deviation value of the pixel is less than 1 sigma or greater than 3 sigma, the mean pixel value is not assigned to the pixel. If the deviation value of the pixel is between 1 sigma and 3 sigma, the mean pixel value for the set of pixels neighboring the pixel is assigned to the pixel to replace the original value of the pixel (e.g., as computed during image reconstruction).

In some embodiments, a non-linear filter may be applied to the image in addition to the outlier filter and/or instead of applying the outlier filter. The non-linear filter is intended to preserve edges in the image while filtering noise in the image by reducing and/or redistributing the noise in the image. By way of example, the non-linear filter may comprise a diffusion filter configured to compute the difference between a value of a first pixel and a mean pixel value of pixels neighboring the first pixel. In some embodiments, if the value of the first pixel is greater than the mean pixel value, at least some of the difference is distributed to the pixels neighboring the first pixel (e.g., causing the value of the first pixel to decrease while the respective values of one or more pixels neighboring the first pixel increase). In this way, a portion of a signal represented by the first pixel of the image is distributed to a set of one or more pixels neighboring the first pixel, for example.

In some embodiments, a degree of diffusion (e.g., a percentage of the difference distributed and/or the number of pixels across which the difference is distributed) is defined by a set of parameters. Further, as will be explained in more detail below, the degree of diffusion may change over the course of several iterations (e.g., during a first iteration, 4% of the difference is diffused, during a next iteration, another 3% of the original difference is diffused, etc.).

It may be appreciated that while the diffusion filtering technique is described with respect to merely a first pixel, such a technique may be applied to a plurality of pixels, such as respective pixels of the image. Moreover, it may be appreciated that a diffusion filter is merely one example type of non-linear filter and that other types of non-linear filters are also contemplated. For example, in another embodiment, the non-linear filter comprises a wavelet filter, which uses various filters (e.g., various stages of high pass filters, low pass filters, etc.) to process data associated with high spatial frequency samples differently than data associated with low spatial frequency samples.

At 210 in the example method 200, the noise contribution to the filtered image (e.g., referred to herein at times as a second noise contribution) is estimated to approximate how much noise remains after the image has been filtered to generate the filtered image. In some embodiments, the noise contribution is estimated using a robust median estimator or other noise estimation technique (e.g., as further described with respect to estimating the first noise contribution at 206).

At 212, the target noise contribution derived at 206 is compared to the second noise contribution estimated at 210 to determine whether the target noise contribution has been satisfied by the filtering. That is, the second noise contribution is compared to the target noise contribution to determine whether a desired amount of noise has been removed from the image received at 204.

When, responsive to the comparing, the target noise contribution has been satisfied, the first filtered image is combined (e.g., blended) with the image to generate a blended image at 212. The blended image represents a blending of the pixels of the first filtered image with the pixels of the image received at 204. By way of example, in some embodiments, a value of a first pixel of the image received at 204 is averaged with a value of a corresponding pixel of the first filtered image to determine a value for a first pixel of the blended image.

In some embodiments, the first filtered image and the image received at 204 are blended using a weighted average, where a percent contribution to the blended image by the first filtered image is the same as or different than a percent contribution by the image received at 204. By way of example, in some embodiments, the user may specify a desired contribution, or weight, of the first filtered image and/or the original image to the blended image. If the user specifies a 20% contribution by the first filtered image, respective pixels of the blended image are determined by weighting the pixels of the image received at 204 by 80% to generate a first weighted image and weighting the pixels of the first filtered image by 20% to generate a second weighted image. The first weighted image and the second weighted image may be subsequently merged to generate the blended image. Accordingly, the value for the first pixel of the blended image corresponds to the value of the first pixel of the image received at 204 multiplied by a weighting factor of 80% combined (e.g., summed together) with the value of the corresponding pixel of the first filtered image multiplied by a weighting factor of 20%. In some embodiments, the user may readjust the desired contribution of the first filtered image on the fly to change the visibility of noise in the blended image.

When, responsive to the comparing, the target noise contribution has not been satisfied, the first filtered image is filtered to generate a second filtered image using one or more of the techniques used to filter the image at 208. Further, a third noise contribution to the second filtered image is estimated using one or more of the estimation techniques used to estimate the second noise contribution at 210, and the third noise contribution is compared to the target noise contribution to determine if the additional filtering has caused the noise contribution to be satisfied. Such a process may be repeated until the target noise contribution is satisfied, at which point the most recently generated filtered image may be blended with the image received at 204 to generate the filtered image.

Figure 3:
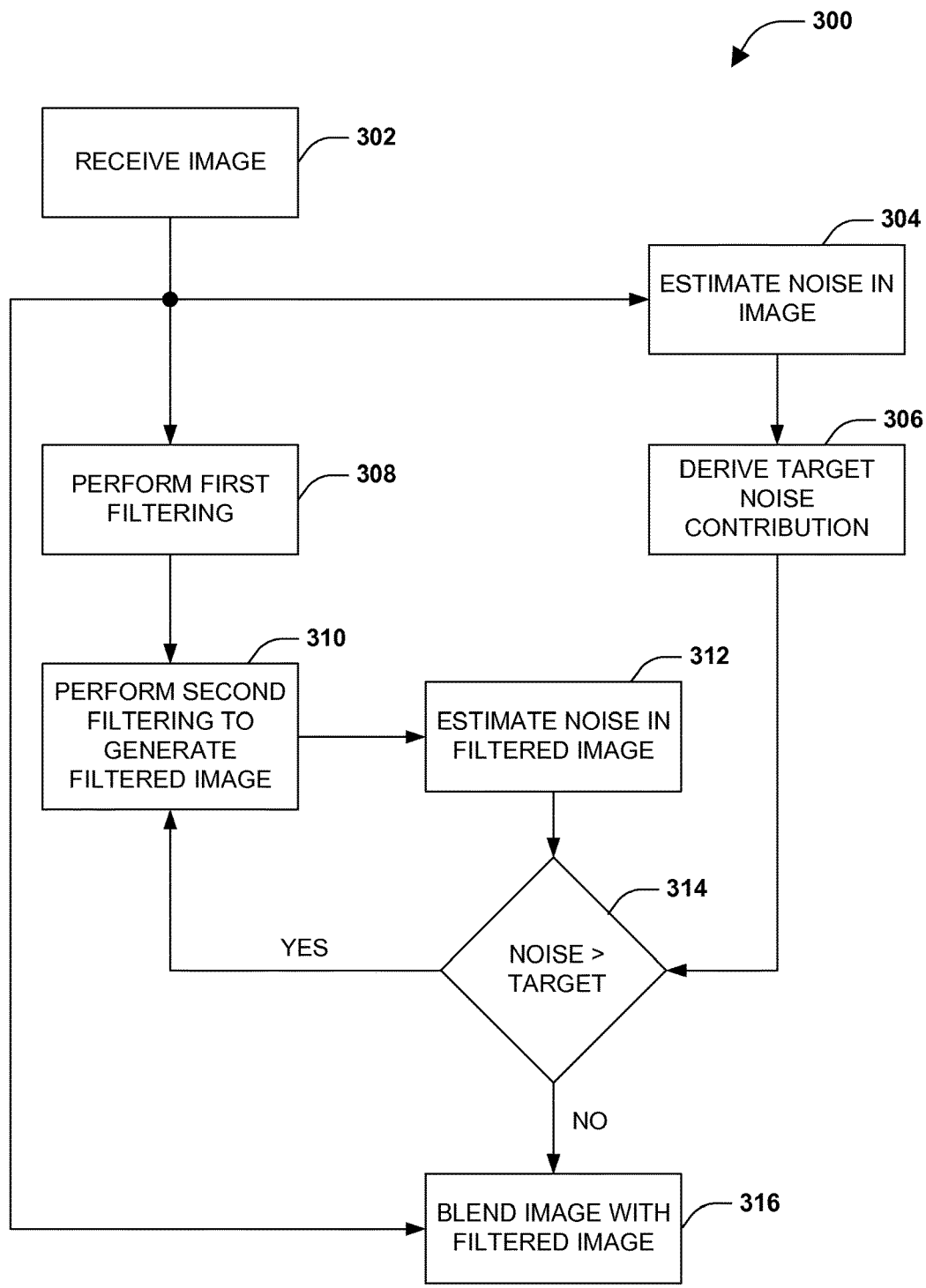
FIG. 3 is a flow diagram illustrating an example method for processing images yielded from an examination via radiation.

Referring to FIG. 3, a flow diagram of an example method 300 for filtering an image yielded from a radiation examination of an object is provided. For purposes of brevity, features of FIG. 3 that are described with respect to FIG. 2 are not described in detail with respect to FIG. 3.

The example method 300 begins at 302 when an image is received. The image is a post-reconstruction image and may comprise artifacts due to photon noise, due to electronic noise, and/or due to the process of reconstructing an image from projection space (e.g., from sine waves).

At 304 in the example method 300, noise in the image is estimated and a target noise contribution (e.g., a desired percentage reduction in noise) is derived from the noise estimation at 306. In some embodiments, the noise is estimated merely based upon pixels having a value within a range that is expected for tissue (e.g., thus excluding pixels representative of non-tissue from the estimation).

At 308 in the example method 300, a first filtering technique is performed on the image to generate an intermediary image. In some embodiments, the first filtering technique is an outlier filtering technique, such as a 3D outlier filtering technique that replaces the value for outlying pixels (e.g., pixels that deviate from a threshold by a deviation threshold). For example, the 3D outlier filtering technique may use a pixel neighborhood around respective pixels to replace outliers with a weighted sum and/or mean pixel value of the neighbors. The mean pixel value may include a value of the pixel and/or may exclude this value when computing the mean pixel value.

In some embodiments, the first filtering technique discriminates between pixels based upon the value of the pixel (e.g., and thus a feature of the object that is likely represented by the pixel). For example, the mean pixel value may be applied to some pixels that deviate from the mean pixel value by a first value while not applying the mean pixel value to other pixels that deviate from the mean pixel value by the first value because the threshold for what is considered an outlier may be different for different pixels. For example, where the pixel has a value of 200 HU (e.g., and thus likely to be indicative of non-tissue) a greater variance between the pixel and neighboring pixels may be deemed acceptable than would be acceptable if the pixel had a value of 50 HU (e.g., and thus likely to be indicative of tissue), because characteristics of non-tissue are likely to cause greater natural variation in pixel values representative of the non-tissue than in pixels representatives of tissue (e.g., which may have little to no variation in density characteristic, z-effective characteristic, etc.).

At 310 in the example method 300, a second filtering technique is performed on the intermediary image to generate a filtered image. The second technique may comprise a diffusion technique, such as an anisotropic diffusion technique, that diffuses (e.g., distributes) a portion of a pixel to a neighborhood of pixels around the pixel. As another example, a wavelet technique may be performed on the image to generate the filtered image.

In some embodiments, whereas the first filtering technique performed at 308 may discriminate between pixels based upon pixel value (e.g., and thus based upon whether the pixel likely represents tissue or non-tissue), the second filtering technique may treat respective pixels the same. Thus, the degree of diffusion for a pixel, for example, may not be dependent upon whether the pixel is likely to be representative of non-tissue or tissue. Rather, the degree of diffusion may be based upon a difference between the value of the pixel relative to the mean pixel value of a set of pixels neighboring the pixel, and desired scope of diffusion (e.g., across how many neighboring pixels the difference is to be distributed, etc.).

At 312 in the example method 300, noise in the filtered image is estimated. In some embodiments, the noise is estimated merely based upon pixels of the filtered image that correspond to pixels of the image received at 302 that were used to estimate noise in the image (e.g., such that pixels likely to be representative of non-tissue are excluded from the estimate).

At 314 in the example method 300, the estimated noise in the filtered image is compared to the target noise contribution to determine if the target noise contribution has been satisfied. For example, the estimated noise in the filtered image is compared to the estimated noise in the image received at 302 to determine if there has been a 20% reduction in noise (e.g., where 20% reduction corresponds to the target noise contribution). When the estimated noise in the filtered image exceeds the target noise contribution, and thus the target noise contribution is not satisfied, the filtered image is transmitted to the second filter, where the second filtering technique is performed on the filtered image to generate a second filtered image.

In some embodiments, where a portion of the method 300 is iteratively repeated by sending the filtered image back to the second filter, one or more parameters of the second filtering technique are adjusted between one or more iterations. By way of example, during a first iteration, when the intermediary image is filtered to generate a first filtered image, the second filtering technique may apply a level 1 diffusion to the intermediary image (e.g., where a portion of the difference between the first pixel and the mean pixel value is distributed merely to immediately adjacent pixels). During a second iteration, when the first filtered image is filtered to generate a second filtered image, the second filtering technique may apply a level 2 diffusion to the first filtered image (e.g., where a portion of the difference between the first pixel and the mean pixel value is distributed to pixels separated from the first pixel by no more than 1 pixel). As another example, the amount of the difference between the value of a pixel and the mean pixel value that is diffused may differ between iterations. For example, during the first iteration, 10% of the difference between a first pixel of the intermediary image and a mean pixel value for pixels neighboring the first pixel may be diffused. During a next iteration, 5% of the difference between a pixel of the first filtered image corresponding to the first pixel of the intermediary image and a mean pixel value for pixels neighboring the pixel may be diffused. In some embodiments, a scope of diffusion (e.g., a number of pixels across which the difference is distributed) and/or an extent of diffusion (e.g., percent of the difference that is distributed) may be variable based upon image features (e.g., which can be measured based upon image gradient and/or a CT value of respective pixels). By way of example, the scope and/or extent of diffusion for an image depicting mostly organs may be different than the scope and/or extent of diffusion for an image depicting mostly bones and/or other non-tissue.

When the estimated noise in the filtered image does not exceed the target noise contribution, and thus the target noise contribution is satisfied, the filtered image (e.g., the most recently generated filtered image) is blended with the image to generate a blended image at 316. The blended image represents a merging of the filtered image with the image and may be presented to the user for inspection. Moreover, in some embodiments, the user may adjust a contribution of the filtered image to the blended image to alter features of the blended image. For example, a first blended image may be generated with a 20% contribution of the filtered image and an 80% contribution of the original image. If the user does not like the appearance of the first blended image (e.g., because edges have been too smoothed by the filtering, etc.) the user may request that a second blended image be generated having less contribution from the filtered image. For example, the second blended image may be generated with a 10% contribution of the filtered image and a 90% contribution of the original image.

Figure 4:
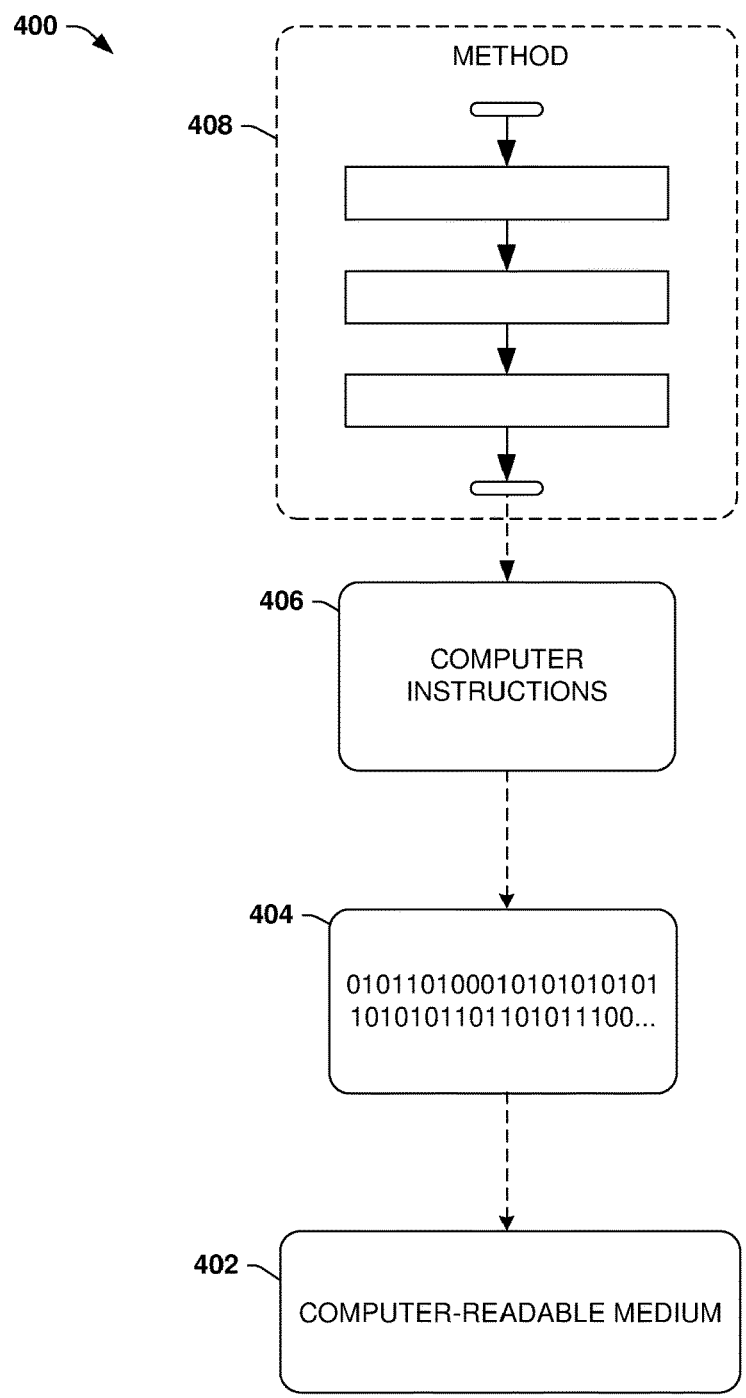
FIG. 4 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 4, wherein the implementation 400 comprises a computer-readable medium 402 (e.g., a flash drive, CD-R, DVD-R, application-specific integrated circuit (ASIC), field-programmable gate array (FPGA), a platter of a hard disk drive, etc.), on which is encoded computer-readable data 404. This computer-readable data 404 in turn comprises a set of processor-executable instructions 406 configured to operate according to one or more of the principles set forth herein. In one such embodiment 400, the processor-executable instructions 406 may be configured to perform a method 408 when executed via a processing unit, such as at least some of the example method 200 of FIG. 2 and/or at least some of example method 300 of FIG. 3. In another such embodiment, the processor-executable instructions 406 may be configured to implement a system, such as at least some of the example radiation imaging system 100 of FIG. 1. Many such computer-readable media may be devised by those of ordinary skill in the art that are configured to operate in accordance with one or more of the techniques presented herein. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this disclosure, "or" is intended to mean an inclusive "or" rather than an exclusive "or." In addition, "a" and "an" as used in this disclosure are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used, such terms are intended to be inclusive in a manner similar to the term "comprising." The claimed subject matter may be implemented as a method, apparatus, or article of manufacture (e.g., as software, firmware, hardware, or any combination thereof).

As used in this disclosure, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first channel and a second channel generally corresponds to channel A and channel B or two different or two identical channels or the same channel.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method for processing images yielded from an examination via radiation, comprising:
   receiving an image of an object that has been exposed to radiation, the image generated based upon an interaction between the radiation and the object;
   sorting a plurality of pixels of the image into a first group of pixels or a second group of pixels according to a value of each pixel of the plurality of pixels;
   estimating a noise contribution of the image based, at least in part, on the value of each pixel of the first group of pixels;
   obtaining a target noise contribution based, at least in part, on the estimated noise contribution of the image;
   filtering the image, the filtering comprising:
      setting a deviation threshold for a first pixel of the plurality of pixels, wherein the setting comprises:
         setting the deviation threshold to a first deviation threshold value responsive to observing that a value of the first pixel is within a first pixel value range; or
         setting the deviation threshold to a second deviation threshold value responsive to observing that the value of the first pixel is within a second pixel value range, the second pixel value range different than the first pixel value range and the second deviation threshold value different than the first deviation threshold value;
      computing a mean pixel value for a set of one or more pixels of the plurality of pixels neighboring the first pixel;
      comparing the mean pixel value to a value of the first pixel to determine a deviation value; and
      applying the mean pixel value to the first pixel when the deviation value exceeds the deviation threshold;
   obtaining a filtered image responsive to the filtering;
   estimating a noise contribution of the filtered image;
   comparing the target noise contribution to the noise contribution of the filtered image;
   observing that the target noise contribution has been satisfied by the filtering; and
   combining the filtered image with the image.

2. The method of claim 1, wherein the estimating the first noise contribution based upon the value of each pixel in the first group of pixels comprises computing spatial derivatives of at least some of the plurality of pixels in at least one dimension of the image.

3. The method of claim 1, wherein the combining comprises:
   applying a first weight to the first filtered image to generate a first weighted image;
   applying a second weight to the image to generate a second weighted image, the second weight different than the first weight; and
   merging the first weighted image with the second weighted image.

4. The method of claim 3, comprising determining at least one of the first weight or the second weight based upon user input.

5. The method of claim 1, wherein the filtering comprises distributing a portion of a signal corresponding to a first pixel of the plurality of pixels to a set of one or more pixels of the plurality of pixels neighboring the first pixel.

6. The method of claim 5, comprising:
   filtering the first filtered image when, responsive to the comparing, the target noise contribution has not been satisfied by the filtering.

7. The method of claim 6, wherein filtering the first filtered image comprises:
   distributing a second portion of the signal corresponding to the first pixel to a second set of one or more pixels of the plurality of pixels neighboring the first pixel, wherein the set of one or more pixels is different than the second set of one or more pixels.

8. The method of claim 7, wherein the set of one or more pixels comprises pixels immediately adjacent the first pixel and the second set of one or more pixels comprises pixels separated from the first pixel by no more than one pixel.

9. The method of claim 1, wherein the value of each of the plurality of pixels corresponds to a computed tomography (CT) value of each of the plurality of pixels.

10. The method of claim 1, further comprising: observing that the target noise contribution has not been satisfied by the filtering responsive to the comparing;
   filtering the filtered image to generate a second filtered image;
   estimating a noise contribution of the second filtered image; and
   comparing the target noise contribution to the estimated noise contribution of the second filtered image;

wherein the observing that the target noise contribution has been satisfied by the filtering comprises: observing that the target noise contribution has been satisfied by the filtering of the filtered image.

11. The method of claim 10, comprising:
combining the second filtered image with the image when, responsive to the comparing the target noise contribution to the third noise contribution, the target noise contribution has been satisfied by the filtering the first filtered image.

12. The method of claim 1, wherein the image is a three-dimensional image.

13. The method of claim 1, wherein:
the estimating the noise contribution of the image comprises computing a first spatial derivative of the value of a first pixel of the image; and
the estimating the noise contribution of the filtered image comprises computing a second spatial derivative of an updated value of a first pixel of the filtered image that corresponds to the first pixel of the image.

14. The method of claim 13, wherein the computing a second spatial derivative comprises computing a derivative of the updated value of the first pixel of the first filtered image in at least two dimensions.

15. A non-transitory computer-readable medium comprising processor-executable instructions that when executed perform a method, comprising:
sorting a plurality of pixels of an image yielded from a radiation examination of an object into a first group of pixels or a second group of pixels according to a value of each pixel of the plurality of pixels;
estimating a noise contribution of the image based, at least in part, on the value of each pixel of the first group of pixels;
obtaining a target noise contribution based, at least in part, on the estimated noise contribution of the image;
filtering the image, the filtering comprising:
setting a deviation threshold for a first pixel of the plurality of pixels, wherein the setting comprises:
setting the deviation threshold to a first deviation threshold value responsive to observing that a value of the first pixel is within a first pixel value range;
or
setting the deviation threshold to a second deviation threshold value responsive to observing that the value of the first pixel is within a second pixel value range, the second pixel value range different than the first pixel value range and the second deviation threshold value different than the first deviation threshold value;
computing a mean pixel value for a set of one or more pixels of the plurality of pixels neighboring the first pixel;
comparing the mean pixel value to a value of the first pixel to determine a deviation value; and
applying the mean pixel value to the first pixel when the deviation value exceeds the deviation threshold;
obtaining a filtered image responsive to the filtering;
estimating a noise contribution of the filtered image;
comparing the target noise contribution to the estimated noise contribution of the filtered image;
observing that the target noise contribution has been satisfied by the filtering; and
combining the filtered image with the image.

16. The non-transitory computer-readable medium of claim 15, wherein the combining comprises:
applying a first weight to the first filtered image to generate a first weighted image;
applying a second weight to the image to generate a second weighted image, the second weight different than the first weight; and
merging the first weighted image with the second weighted image.

17. The non-transitory computer-readable medium of claim 15, wherein the image is a three-dimensional (3D) image.

18. The non-transitory computer-readable medium of claim 15, wherein the filtering comprises distributing a portion of a signal corresponding to a first pixel of the image to a set of one or more pixels of the image neighboring the first pixel.

19. The non-transitory computer-readable medium of claim 18, the method comprising:
filtering the first filtered image when, responsive to the comparing, the target noise contribution has not been satisfied by the filtering; and
distributing a second portion of the signal corresponding to the first pixel to a second set of one or more pixels of the plurality of pixels neighboring the first pixel, wherein the set of one or more pixels is different than the second set of one or more pixels.

20. A radiation imaging system, comprising:
a radiation source configured to expose an object under examination to radiation;
a detector array configured to produce one or more signals based upon detecting at least some of the radiation that traverses the object;
an image reconstruction component configured to reconstruct an image based upon the one or more signals; and
a noise reduction component configured to:
sort a plurality of pixels of the image into a first group of pixels or a second group of pixels according to a value of each of the plurality of pixels;
estimate a first noise contribution to the image to derive a target noise contribution, wherein the estimate is computed based upon the value of each pixel in the first group of pixels;
filter the image to generate a first filtered image by:
setting a deviation threshold for a first pixel of the plurality of pixels, wherein the setting comprises:
setting the deviation threshold to a first deviation threshold value when a value of the first pixel is within a first pixel value range; and
setting the deviation threshold to a second deviation threshold value when the value of the first pixel is within a second pixel value range, the second pixel value range different than the first pixel value range and the second deviation threshold value different than the first deviation threshold value;
computing a mean pixel value for a set of one or more pixels of the plurality of pixels neighboring the first pixel;
comparing the mean pixel value to a value of the first pixel to determine a deviation value; and
applying the mean pixel value to the first pixel when the deviation value exceeds the deviation threshold;
estimate a second noise contribution to the first filtered image;
compare the target noise contribution to the second noise contribution to determine whether the target noise contribution has been satisfied by filtering the image to generate a first filtered image; and combine the first filtered image with the image when, responsive to comparing the target noise contribution to the second noise contribution, the target noise contribution has been satisfied by filtering the image to generate a first filtered image.

\* \* \* \* \*